United States Patent [19]
Jeyendran

[11] Patent Number: 5,536,243
[45] Date of Patent: Jul. 16, 1996

[54] TIME-RELEASE INSEMINATION DEVICE

[76] Inventor: Rajasingam S. Jeyendran, 1845 Golden Pond La., Wheaton, Ill. 77024

[21] Appl. No.: 354,613

[22] Filed: Dec. 13, 1994

[51] Int. Cl.$^6$ .......................... A61B 17/43; A61M 37/00
[52] U.S. Cl. ........................ 600/35; 604/131; 604/55
[58] Field of Search .................. 604/70, 54–55, 604/131, 150, 892.1; 600/35, 33

[56] References Cited

U.S. PATENT DOCUMENTS

| | | |
|---|---|---|
| 372,922 | 11/1887 | McCord . |
| 544,091 | 8/1895 | Gladman . |
| 2,764,975 | 10/1956 | Greenberg . |
| 3,811,423 | 5/1974 | Dickenson . |
| 3,811,443 | 5/1974 | Dickenson . |
| 3,865,108 | 2/1975 | Hardtop . |
| 4,111,202 | 9/1978 | Theeuwes . |
| 4,312,347 | 1/1982 | Magoon et al. . |
| 4,480,642 | 11/1984 | Stoy et al. . |
| 5,318,780 | 6/1994 | Viegas et al. . |

OTHER PUBLICATIONS

Dilapan Hydroscopic Cervical Dilator: Packaging and Instructions for Use, Gynotech, Inc.
Laminaria Cervical Dilator: Packaging and Product Data, Medgyn Products, Inc.
"Slow release intrauterine insemination versus the bolus technique in the treatment of women with cervical mucus hostility"; Human Reproduction vol. 7 No. 2 pp. 227–229, 1992, Nabil S. Muharib, Ahmed Abdel Gadir, and Robert W. Shaw.

Primary Examiner—Randall L. Green
Assistant Examiner—Perry E. Van Over
Attorney, Agent, or Firm—Tilton, Fallon, Lungmus

[57] ABSTRACT

A self-contained time-release artificial insemination device which introduces a bolus of semen into the cervical canal or uterus over a period of hours is disclosed. The device includes a cervical cap adapted to conform and adhere to the cervix and includes an elongated nipple that extends in a perpendicular direction from the cap for insertion into the cervical canal or uterus. A time-release mechanism is provided in communication with the nipple for delivering semen through the nipple and includes a tubular body which defines a semen chamber and expansion chamber. A plunger is slidably mounted in the tubular member for separating the semen and expansion chambers. A reservoir is provided in communication with the expansion chamber for providing a quantity of fluid thereto, and a sealable aperture is provided for withdrawing and introducing fluids to both the reservoir and expansion chamber. Within the expansion chamber, a quantity of water-swellable material is disposed for absorbing water from the reservoir and expanding so that the plunger is urged towards the cervical cap and the semen is discharged through the nipple and into the cervix or uterus over a period of hours.

34 Claims, 2 Drawing Sheets

TIME-RELEASE INSEMINATION DEVICE

BACKGROUND AND SUMMARY

Artificial insemination is commonly used to increase pregnancy rates and overcome fertility problems for humans and is also often used to breed animals for increasing genetic gain by using semen from males with desirable genetics. While many methods and devices are known for achieving artificial insemination, it is believed that many of the known techniques are inconvenient, expensive and have been less than successful in achieving higher pregnancy rates.

In humans artificial insemination is often accomplished by using a pericervical technique in which a cervical cap is filled with 0.5 to 1.0 ml. of semen and placed over the patient's cervix which causes the semen to diffuse and spread evenly over the inside of the cap and over the cervix. This technique is problematic in that only a small portion of the semen is exposed directly to the cervical Os and the majority of the semen expires where it is trapped between the cervix and the cap. Another technique is intrauterine insemination in which semen is directly deposited into the uterus using a pipette and the hostile environment of the cervical canal and mucus is bypassed. This technique is relatively difficult to accomplish, is time-consuming, and requires highly trained personnel to administer the treatment as it involves intrauterine manipulation which has inherent health risks including the potential of causing infection. In addition to its cost and complexity, it has also been found that intrauterine insemination generally does not offer any significant advantage in pregnancy results as compared to cervical insemination. Friedman A, Haas S, Kredenster J, et al., 1989 Int. J. Fertil. 34:199; Nachgigall R. D., Faure N, Glass R. J., 1979 N. Engl. J. Med. 32:141; Peters A. J., Hecht B, Wents A. L., et al., 1993 Fertil. Steril. 59:121.

In animals artificial insemination is often accomplished by vaginal insemination, cervical insemination or intrauterine insemination, which all suffer from their own complexities and problems. In particular, vaginal insemination involves depositing a sample or bolus of semen into the anterior vagina and this technique generally does not increase pregnancy rates beyond that associated with natural insemination. Cervical insemination is probably the most successful method of inseminating animals and it involves introducing semen into the cervical canal or uterus with a pipette which is inserted as deep as possible into the cervix without using force. While this method has been effective for artificially inseminating dairy cattle, it is impractical for use with many types of animals. For example, the cervical canal of sheep is closed by reciprocal folds and depressions of the mucus membrane which prevent insertion of a pipette into the cervix to any depth. For such animals, intrauterine insemination is an option but that technique is performed laparoscopically under anesthesia which requires trained personnel, is expensive and time consuming, and has a potential risk to the animal. Despite the complexities and expense associated with that technique, it is growing in popularity for inseminating sheep as there is a strong desire to take advantage of the genetic gain offered by artificial insemination which has been successfully utilized in other breeding programs such as for dairy cattle.

A recent study has demonstrated that a significantly higher rate of pregnancy can be achieved by intrauterine insemination which is administered over a period of time, such as three hours, than when insemination is performed by simply introducing a bolus of sperm into the uterus. Muharib N. S., Gadir A. A., Shaw R. W., 1992 Human Reprod. 7:227. While it has been recognized that slow introduction of semen into the uterus enhances the rate of pregnancy, the technique used in the noted study is inconvenient and expensive for use with humans and is impractical for use with animals. In particular, the technique involved having the patient lie supine on a bed for a period of hours and a plastic tube was introduced into the uterine cavity after exposing the cervix with a bivalve speculum. The speculum was then removed and the tube was attached to a slow-release auto-syringe with an auto-syringe driver placed on the bed beside the patient. The study notes that many of the patients were initially apprehensive towards use of an intrauterine catheter. The study proposes that the disadvantages of the technique could be lessened by using a self-retaining intrauterine catheter in which the pump or driver is strapped to the patient's leg. However, the proposed system is still complex, results in limited patient mobility, and is unrealistic as an option for breeding animals.

Other attempts have been made in the prior art to provide a time-release insemination device such as exemplified in Dickinson U.S. Pat. No. 3,811,443. Dickinson discloses a device having a complicated anchoring assembly for securing the device in a vaginal canal which presents problems of patient comfort and acceptance. The means for expelling semen from the device into the cervical canal also present problems. One embodiment discloses the use of seeds which emit carbon dioxide to develop a pressure in the device to discharge the semen. However, it is believed that such a device would not develop a sufficient pressure to overcome the resistant forces of the mucus in the cervical canal for successful delivery of the semen. Dickinson also proposes using dry ice (solid carbon dioxide) to expel the semen but is believed that the expense and complications encountered with handling dry ice renders such a construction impractical for widespread use. The device is also complicated with respect to filling the device with semen and loading the expansion chamber.

An important aspect of this invention therefore lies in providing an insemination device which administers semen to the cervical canal or uterus over a period of hours and has a simple and efficient construction that may be easily used with humans or for breeding animals. Such results are achieved by providing a device with a cervical cap which conforms and adheres to the patient's cervix and which includes an elongated nipple for insertion into the cervix or uterus for intracervical or intrauterine insemination. A self-contained time-release mechanism is provided in communication with the nipple for discharging semen through the nipple and into the cervix or uterus over a period of hours. The mechanism includes a tubular member which defines a semen chamber in communication with the nipple and an expansion chamber which is separated from the semen chamber by a plunger. The expansion chamber is filled with a water-swellable material and is attached to a resilient, collapsible reservoir which supplies fluid to the water-swellable material. In use, the device is inserted into the vaginal canal of the patient and the cervical cap fits snugly over the patient's cervix to retain the device in position. Over a period of hours, the water-swellable material in the expansion chamber draws or absorbs fluid from the reservoir and expands so that the plunger is urged towards the cervix and causes a slow time-release discharge of semen through the nipple and into the cervix or uterus.

In brief, the time-release insemination device of this invention comprises a dome-shaped cervical cap adapted to conform and adhere to a cervix and having a peak portion at one end and a generally circular periphery at the other end. An elongated tubular nipple which defines a passageway extends from the peak portion of the cap in a perpendicular direction towards the circular periphery for insertion into the cervical canal or uterus. For animals having a generally unobstructed cervical canal, the nipple preferably has a distal end which extends beyond the circular periphery of the cap to discharge semen into the middle or posterior end of the cervical canal or uterus so that the hostile environment of the cervical mucus is bypassed. For animals having a obstructed cervical canal, the nipple preferably has a distal end which does not project beyond the circular periphery of the cap so the nipple is positioned directly adjacent to the cervical Os. The time-release mechanism includes an elongated tubular member that defines a semen chamber which is in fluid communication with the nipple's passageway and defines an expansion chamber which is separated from the semen chamber by a plunger slidably mounted therein. Reservoir means are provided in fluid communication with the expansion chamber for providing a quantity of fluid thereto. Within the expansion chamber, expansion means are disposed for absorbing fluid from the reservoir means and expanding so that the plunger is urged towards the cervical cap to cause discharge of semen from the semen chamber through the passageway of the nipple and into the cervical canal or uterus.

The device preferably includes sealable aperture means which are in communication with the expansion chamber and the reservoir means for allowing withdrawal or introduction of fluids therefrom or thereto. Such sealable aperture means may take the form of known self-sealing elements or injection sites commonly used in the medical industry. The reservoir means is preferably constructed of a resilient balloon-shape reservoir which defines an interior volume and is operable between a collapsed state in which the volume is evacuated and an expanded state in which the volume is filled with fluid. Such a construction facilitates filling the semen chamber with semen and filling the reservoir with fluid without causing premature discharge of semen from the device. More specifically, withdrawal of fluid through the self-sealing aperture evacuates and collapses the reservoir and draws the plunger towards the distal end of the tubular member to create a negative pressure in the semen chamber and passageway of the nipple for drawing semen into the device. Once the semen chamber is filled and the reservoir is collapsed, fluids such as water can be introduced through the self-sealing aperture to fill the collapsed reservoir back to an expanded state without the fluid significantly entering the expansion chamber and causing premature movement of the plunger or unnecessary discharge of semen.

In an alternate construction, the sealable aperture means may take the form of a self-sealing element or injection site as previously described and a unidirectional valve also provided in communication with the reservoir means and the expansion chamber. In such a construction, the reservoir means may be collapsed by squeezing the reservoir between a user's fingers so that the air or fluid in the reservoir is evacuated through the unidirectional valve. Thereafter, the distal end of the nipple is inserted into a quantity of semen and the collapsed, resilient reservoir is released so that it resumes its expanded state and creates a vacuum which draws the plunger towards the distal end of the tubular member, thereby drawing semen into the nipple. Once the semen chamber is filled and the reservoir is expanded, fluid such as water is introduced through the self-sealing element to fill the reservoir while the air already in the reservoir is allowed to escape through the unidirectional valve. The unidirectional valve is preferably positioned on the tubular member adjacent to the expansion chamber.

The expansion means preferably take the form of a water-swellable material and alginates or seaweed have been found to be particularly suitable of this purpose. Laminaria seaweed is believed to be preferable as it slowly expands over a period of hours when exposed to water. However, other suitable hydrocholoids which provide a slow release of semen through the device may also be effective. Preferably, the device releases the semen over a period of at least 3 hours, preferably 6–8 hours.

The cervical cap may also be provided with release means for minimizing surface adhesion between the cervical cap and cervix, and the release means may take the form of a plurality of holes formed in the cervical cap which reduce its surface area. The reduction in surface adhesion between the cervical cap and the cervix facilitates removal of the device after the semen has been deposited. Conversely, it may be desirable in some applications to provide the cervical cap with improved retention capabilities, and projection means may be provided on the nipple for engaging the side walls of the cervical canal. Such projection means may take the form of a spirally-extending rib. It is also contemplated that in some embodiments it would be useful to form the cervical cap of a biodegradable or water-soluble material which, after full release of the semen, would sufficiently degrade or dissolve such that it would automatically disengage from the cervix and would be naturally expelled by the animal.

Other features, objects and advantages of the invention will become apparant from the drawings and specifications.

DETAILED DESCRIPTION OF PREFERRED EMBODIMENTS

Figure 1:
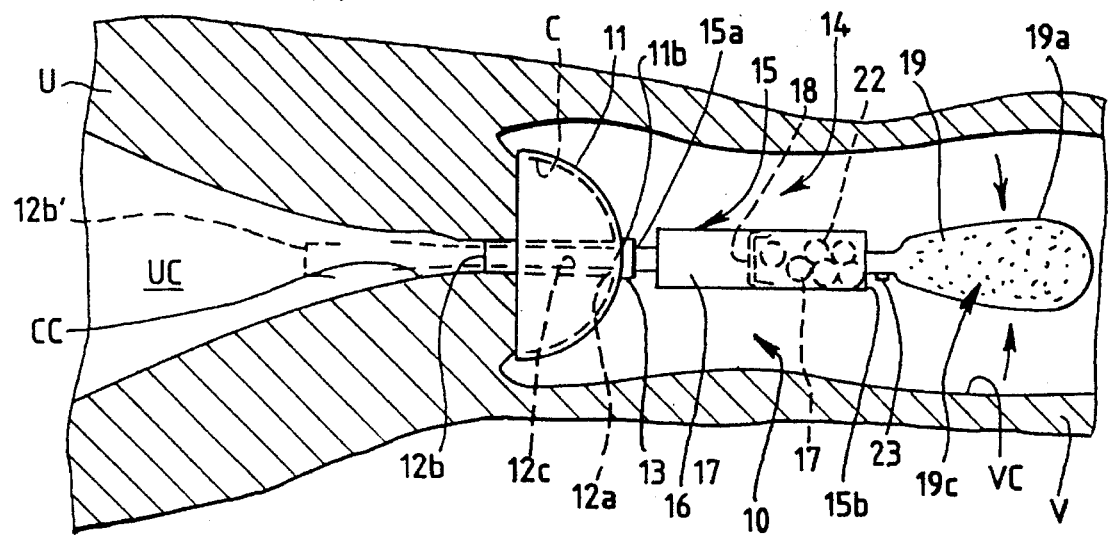
FIG. 1 is a schematic side view of the time-release insemination device of this invention in the environment of the vaginal canal and attached to the cervix.

Referring to the drawings, the numeral 10 generally designates a time-release insemination device which is disposed in the vaginal canal VC of the vagina V. The insemination device includes a dome-shaped cervical cap 11 constructed of a flexible material adapted to conform and adhere to the cervix C by surface adhesion for maintaining the device in communication with the cervical canal CC which leads to the uterine cavity UC of the uterus U. Cervical cap 11 includes a circular periphery 11a which surrounds and fits over the cervix and a peak portion 11b which is positioned adjacent to the cervical Os or entrance. The cervical cap may be formed from any medical grade plastic such as polyethylene or other known materials commonly used for constructing cervical caps.

An elongated cylindrical nipple 12 includes proximal and distal ends 12a and 12b and extends outward from peak portion 11b of the cervical cap in a generally axial direction. However, the nipple is somewhat flexible and may be bent or flexed so that it will fit into the cervical canal without stressing the cervical cap. In the illustration given in FIG. 1, distal end 12b of the nipple projects beyond the circular periphery 11a of the cap and is positioned in the patient's cervical canal CC. Such a construction is advantageous for use with patients or animals whose anatomy will physically accommodate such a nipple as the semen bypasses the hostile environment of the cervical mucus and is introduced in close proximity to the uterus. In an alternate construction, nipple 12 may be extended so that distal end 12b' (shown in phantom) projects past the cervical canal and into the uterine cavity UC for intrauterine insemination.

Figure 4:
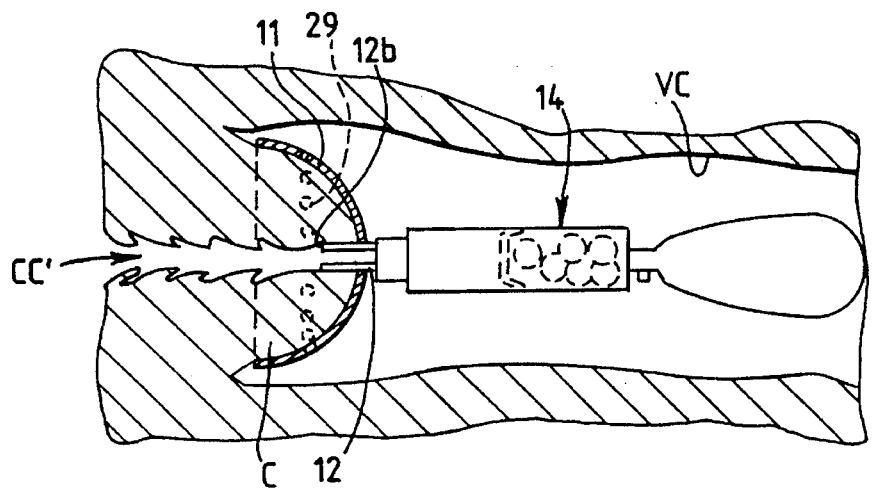
FIG. 4 is a schematic side view of an alternate embodiment of the instrument in the environment of the vaginal canal and attached to a cervix of an animal having a cervical canal characterized by reversing folds and depressions.

For applications in which the anatomy of the animal limits the extent that the nipple can be physically inserted past the Os, the nipple may be shortened, as shown in FIG. 4, so that the distal end of the nipple does not project beyond the peripheral edge of the cap. In such a construction, the distal end projects just beyond the Os and terminates just before the cervical canal CC' is obstructed such as by reciprocal folds and depressions commonly found in the cervical canals of animals such as sheep.

Nipple 12 defines a passageway 12c that extends from the nipple's distal to proximal end. The nipple's proximal end 12a includes a hub 13 for connection to a time-release mechanism, generally designated at 14, which discharges semen through the passageway of the nipple and into the cervical canal or uterine cavity. The time-release mechanism includes an elongated hollow tubular member 15 having a proximal end 15a attached to hub 13 by threads 13a (FIG. 2 and 3) or other suitable connection means and having an opposite distal end 15b. In the alternative, nipple 12 and tubular member 15, as well as cap 11, may be formed from a one-piece construction such as by integral molding. Tubular member 15 defines a semen chamber 16 at its proximal end which is in fluid communication with passageway 12c and defines an expansion chamber 17 at its distal end which is separated from the semen chamber by a plunger 18. Plunger 18 is slidably mounted in tubular member 15 for axial movement therein and is operable to discharge semen from the semen chamber through passageway 12c of the nipple when the plunger is urged towards the proximal end of the tubular member.

Figure 2:
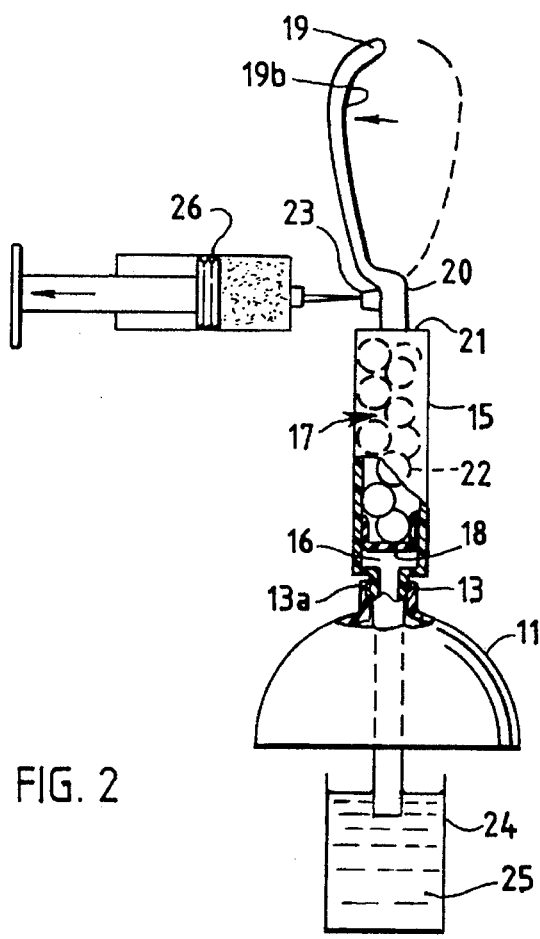
FIG. 2 is a schematic, partially cross-sectional, side view of the instrument.

Reservoir means are provided in fluid communication with the expansion chamber for providing a quantity of fluid thereto. The reservoir means may take the form of a collapsible balloon-shaped reservoir 19. Reservoir 19 is constructed of a resilient material such as natural or synthetic rubbers so that it is operable between an expanded state 19a as shown in FIG. 1 and a collapsed state 19b as shown in FIG. 2. In the embodiment shown in the illustrations, reservoir 19 is connected by a stem 20, which may be integrally formed with reservoir 19, to an endplate 21 which is secured in the distal end of tubular member 15 by threads or other suitable attachment means (not shown). However, it will be understood that other suitable reservoir means and means for attaching same to the expansion chamber may be utilized within the scope of this invention.

Within expansion chamber 17, expansion means 22 are provided for absorbing fluid from reservoir 19 so that the expansion means swells or expands and urges plunger 19 towards the proximal end 15a of the tubular member. Such movement of plunger 19 causes semen in semen chamber 16 to pass through passageway 12b of nipple 12 so that it is released into the adjacent cervix or uterus. The expansion means preferably take the form of a water-swellable material which will gradually absorb water from the reservoir and expand over a period of hours. Water-swellable alginates or seaweed are believed to be preferable for use as the expansion means, and commercially available laminaria (*Laminaria Japonica*) is believed to be particularly suitable due to its slow rate of swelling. Suitable hydrocholoids or other water-swellable materials may also be used which have a sufficiently slow rate of swelling or absorption to be effective. The expansion means or water-swellable material should be provided in a sufficient quantity in the expansion chamber to cause release of the semen through nipple 12 for a period of at least 3 hours, preferably 6–8 hours. It will be understood that sperm typically expire after a period of 48 hours in an environment such as the semen chamber and that release of semen beyond 48 hours is not useful.

Sealable aperture means are provided for allowing withdrawal or introduction of fluids from or into the expansion chamber 16 and reservoir 19. In the illustrations given in FIGS. 1–4, the sealable aperture means take the form of a self-sealing injection site or element 23 of the type commonly used in the medical industry for allowing passage of a syringe needle and then forming a fluid-tight seal upon withdrawal of the needle. However, the sealable aperture means may take the form of other known sealable valves, such as a unidirectional valve, and an alternate embodiment of the sealable aperture means is more fully described in connection with FIGS. 6 and 7 below. Injection site 23 is shown at a location on stem 20 but may be positioned at any location that is in communication with both the expansion chamber 17 and an interior volume 19c of reservoir 19.

Figure 3:
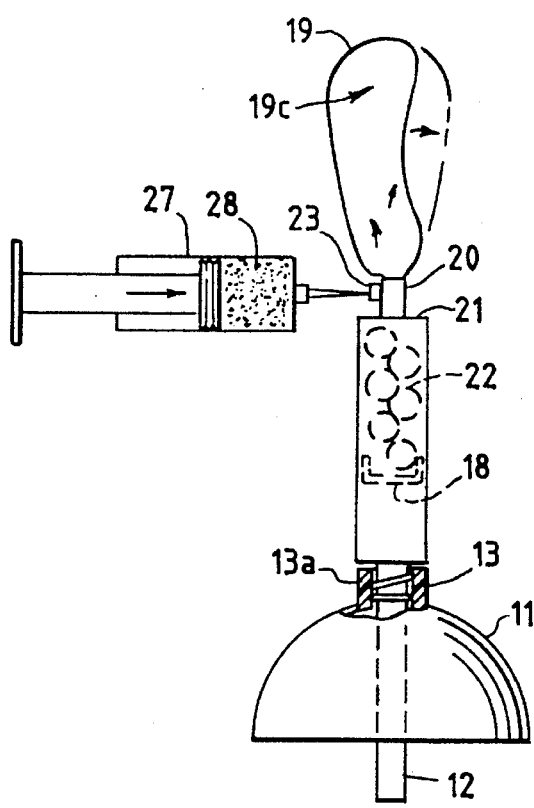
FIG. 3 is a schematic, partially cross-sectional, side view of the instrument.

Preparing the instrument for use is schematically illustrated in FIGS. 2 and 3. First, the device is preassembled with plunger 18 generally at the proximal end of tubular member 15 and with a predetermined quantity of water-swellable material 22 disposed in the expansion chamber. The water-swellable material is loaded in the expansion chamber by removing endplate 21. To fill the semen chamber, nipple 12 is inserted into container 24 which is filled with semen 25, and a syringe 26 is used to withdraw air through self-sealing element 23 from both reservoir 19 and expansion chamber 16. Withdrawal of air from the expansion chamber causes plunger 18 to move towards the tubular member's distal end which creates a negative pressure in the semen chamber and nipple and draws semen 25 from container 24 into the device. Withdrawal of air from reservoir 19 causes the reservoir to assume a collapsed state 19b as shown in FIG. 2.

Once semen chamber 16 is filled and reservoir 19 is collapsed, a second syringe 27 is filled with water 28, and the water is injected through self-sealing element 23 into reservoir 19 until its volume is filled and it assumes its expanded state. The amount of water injected into the instrument should be equal to or slightly greater than the volume of reservoir 19 so that the reservoir is sufficiently filled but only a limited quantity of water flows into expansion chamber 16; otherwise, greater quantities of water could cause movement of plunger 18 and premature discharge of semen 25 through nipple 12. The device is then inserted into the vaginal canal and the cervical cap 11 is secured to the patient's cervix. Over a period of hours, the water-swellable material expands by absorbing water from reservoir 19 and gradually urges plunger 18 towards the nipple, thereby causing a slow release of semen from the nipple into the cervical canal or uterus.

In one construction of the invention, cervical cap 11 is of the standard type and nipple 12 has a length of 2.5 to 3.0 cm. Tubular member 15 has a volume of 3 ml. and reservoir 19 has a volume of 1.2 ml. A 3 ml. syringe with a 22 gauge needle is used to withdraw and introduce fluids through self-sealing element 22. The syringe is used to inject 1.2 ml. of water into reservoir 19. The water-swellable material is laminaria and it causes gradual release of semen through the nipple for a period of at least 3 hours, preferably 6–8 hours.

In the embodiment illustrated in FIG. 4, cervical cap 12 is provided with release means for minimizing surface adhesion between the cervical cap and cervix which facilitates removal of the cap. The release means may take the form of a plurality of holes or apertures 29 in the cap which reduce the surface area of the cap so that surface adhesion between the cap and the cervix is minimized.

For use with animals, cervical cap 11 may be constructed of a biodegradable or water-dissolvable material so that the cap will sufficiently degrade or dissolve after a period of time and disengage itself from the cervix. The device is then naturally expelled by the animal. One such water-dissolvable material is polyvinyl alcohol and it may be adapted to have a dissolution time of greater than 48 hours, or a period greater than the semen release time. In such a construction, cap 11 maintains its structural integrity for a sufficient amount of time so that the semen is introduced into the cervical canal or uterus over a period of hours but the cap will eventually dissolve or weaken so that it disengages from the cervix and can be naturally expelled. Such a construction is advantageous in that the animals do not need to be recaptured for removal of the device by trained personnel.

For use with humans, the entire insemination device may advantageously be constructed so that it is reusable and can be sterilized between uses. However, it will be understood that the device may also be constructed for one-time use as a disposable item.

Figure 5:
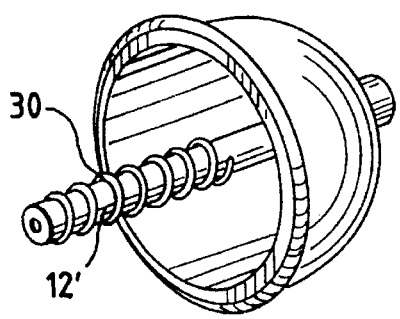
FIG. 5 is a perspective view of an alternate embodiment of a cervical cap used with this invention.

In the embodiment illustrated in FIG. 5, nipple 12' is provided with protrusion means for engaging the interior walls of the cervical canal for improving retention of the device. As illustrated, such projection means may take the form of a spirally-extending rib 30 that wraps around the length of nipple 12'. While such a spirally-extending rib is believed to be advantageous, it will be understood that other protrusions and configurations may be utilized in order to engage the walls of the cervical canal.

Figure 6:
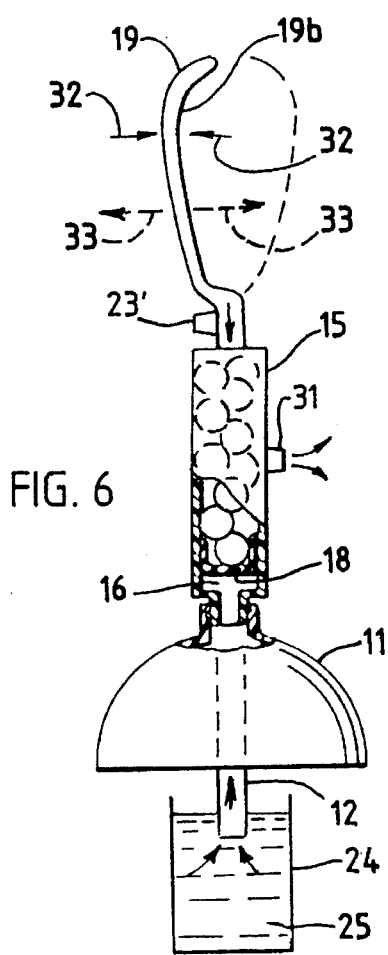
FIG. 6 is a schematic, partially cross-sectional, side view of an alternate embodiment of the instrument.
Figure 7:
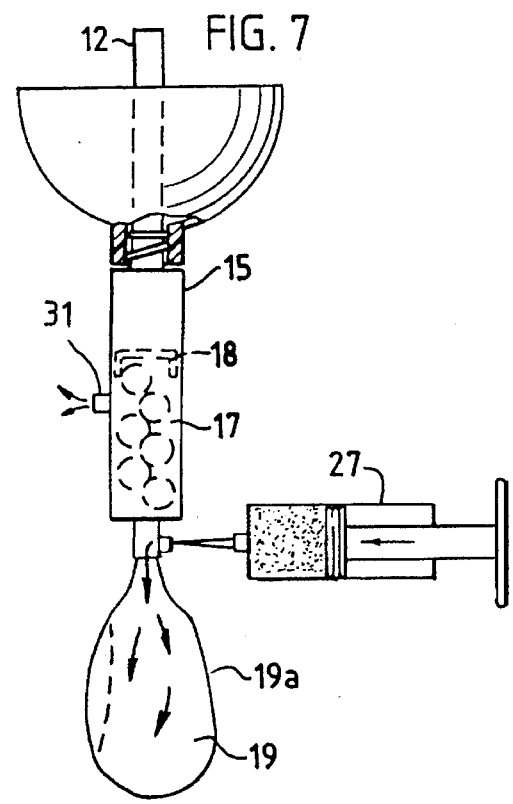
FIG. 7 is a schematic, partially cross-sectional, side view of the alternate embodiment of the instrument illustrated in FIG. 6.

In an alternate construction illustrated in FIGS. 6 and 7, the construction of the insemination device is essentially the same as the previously discussed embodiment except for the sealable aperture means. In the illustrations given in FIGS. 6 and 7, the sealable aperture means take the form of a self-sealing injection site or element 23' and a unidirectional valve 31. In such a construction, reservoir 19 can be evacuated to its collapsed state 19b by squeezing the reservoir between a user's fingers as represented by arrows 32. This forces the air in the reservoir to be expelled through unidirectional valve 31 and also urges plunger 18 towards the proximal end of the tubular member 15. Thereafter, nipple 12 is inserted into a container 25 filled with semen 24 and the resilient reservoir 19 is released so that it expands as represented by dashed line arrows 33. This creates a vacuum in tubular member 15 and draws plunger 18 towards the proximal end of the device so that semen 24 is drawn into the semen chamber 16. Reservoir 19 will also, at least partially, resume its expanded state as it fills with air from the expansion chamber.

Once semen chamber 16 is filled and reservoir 19 resumes its expanded state 19a as illustrated in FIG. 7 (or a partially expanded state), a syringe 27 is used to inject water through self-sealing element 23' into reservoir 19. Introduction of the water through element 23' forces the air in the reservoir to be evacuated through unidirectional valve 31 so that the water replaces the air and the device is ready for use once the reservoir is completely filled. In a preferred construction, unidirectional valve 31 is positioned on tubular member 15 adjacent to and in communication with the expansion chamber 17. In such a construction, the device can be held in a substantially vertical orientation with the nipple pointed upward as shown in FIG. 7 so that, when fluid is injected through element 23' the fluid will gravitate into reservoir 19 and the lighter media, air, will be displaced upwards out of the reservoir and into the expansion chamber 17 where it will escape through the one-way valve 31. It will be understood that the sealable aperture means may take the form of other valve arrangements or systems which facilitate the withdrawal of fluids into the reservoir means and expansion means.

While in the foregoing embodiments of this invention have been disclosed in considerable detail for purposes of illustration, it will be understood that many of these details may be varied without departing from the spirit and scope of the invention.

I claim:

1. A time-release insemination device comprising:
   a dome-shaped cervical cap adapted to conform and adhere to a cervix and having a peak portion at one end and a generally circular periphery at the other end;
   an elongated tubular nipple defining a passageway and extending from said peak portion of said cap in a generally axial direction towards said circular periphery;
   an elongated tubular member having proximal and distal ends and defining a semen chamber at said proximal end which is in fluid communication with said passageway of said nipple and defining an expansion chamber at said distal end;
   a plunger slidably mounted in said tubular member for axial movement therein and positioned to separate said semen chamber from said expansion chamber;
   reservoir means connected to said tubular member and in fluid communication with said expansion chamber for providing a quantity of fluid thereto; and
   expansion means disposed in said expansion chamber for absorbing fluid from said reservoir means and expanding so that said plunger is urged towards said proximal end of said member to cause discharge of semen from said semen chamber through said passageway of said nipple.

2. The insemination device of claim 1 in which sealable aperture means are provided in communication with said expansion chamber and said reservoir means for allowing withdrawal or introduction of fluids from or into said expansion chamber and said expansion means.

3. The insemination device of claim 1 in which said expansion means comprises a water-swellable material.

4. The insemination device of claim 3 in which said water-swellable material comprises an alginate.

5. The insemination device of claim 4 in which said alginate is comprised of laminaria.

6. The insemination device of claim 3 in which said water-swellable material comprises a hydrocolloid.

7. The insemination device of claim 1 in which said nipple includes a distal end which projects beyond said circular periphery of said cap.

8. The insemination device of claim 1 in which said nipple includes a distal end which does not project beyond said circular periphery of said cap.

9. The insemination device of claim 1 in which said expansion means causes said semen to be discharged through said nipple for at least 3 hours.

10. The insemination device of claim 1 in which said expansion means causes said semen to be discharged through said nipple for a period of about 6–8 hours.

11. The insemination device of claim 1 in which said expansion means comprises a water-swellable material.

12. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto;

expansion means disposed in said expansion chamber for absorbing fluid from said reservoir means and expanding so that said plunger is urged towards said proximal end of said member to cause discharge of semen from said semen chamber through said passageway of said nipple; and sealable aperture means provided in communication with said expansion chamber and said reservoir means for allowing withdrawal or introduction of fluids from or into said expansion chamber and said expansion means, said reservoir means defining a volume and being operable between a collapsed state in which said volume is evacuated and an expanded state in which said volume is filled with a fluid; wherein withdrawal of fluid through said sealable aperture means evacuates said volume so that said reservoir means assumes said collapsed state and also draws said plunger in said tubular member towards its distal end, thereby creating a negative pressure in said semen chamber and said passageway of said nipple for drawing semen into said passageway and said semen chamber.

13. The insemination device of claim 12 in which, when said reservoir means is in said collapsed state, introduction of fluid through said sealable aperture means fills said volume of said reservoir means so that it resumes said expanded state without causing movement of said plunger within said tubular member.

14. The insemination device of claim 13 in which said sealable aperture means comprises a self-sealing element.

15. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto;

expansion means disposed in said expansion chamber for absorbing fluid from said reservoir means and expanding so that said plunger is urged towards said proximal end of said member to cause discharge of semen from said semen chamber through said passageway of said nipple; and sealable aperture means are provided in communication with said expansion chamber and said reservoir means for allowing withdrawal or introduction of fluids from or into said expansion chamber and said expansion means, said reservoir means defining a volume and being operable between a collapsed state in which said volume is evacuated and an expanded state in which said volume is filled with a fluid and said sealable aperture means comprises a self-sealing element and a unidirectional valve;

wherein, when said reservoir means is in said expanded state, said reservoir means is collapsible so that said volume is evacuatable through said unidirectional valve and, when said reservoir means is in said collapsed state, said reservoir means is resiliently expandable upon release so that it draws said plunger in said tubular member towards its distal end, thereby creating a negative pressure in said semen chamber and said passageway of said nipple for drawing semen into said passageway and said semen chamber.

16. The insemination device of claim 15 in which, when said reservoir means is in said expanded state or said partially expanded state, introduction of fluid through said self-sealing element causes fluid in said reservoir means to be evacuated through said unidirectional valve so that said introduced fluid replaces said fluid in said reservoir means.

17. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto;

expansion means disposed in said expansion chamber for absorbing fluid from said reservoir means and expanding so that said plunger is urged towards said proximal end of said member to cause discharge of semen from said semen chamber through said passageway of said nipple; and said reservoir means comprising a resilient balloon-shaped reservoir.

18. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto;

expansion means disposed in said expansion chamber for absorbing fluid from said reservoir means and expanding so that said plunger is urged towards said proximal end of said member to cause discharge of semen from said semen chamber through said passageway of said nipple; said nipple having a cylindrical exterior surface and projection means disposed on said exterior surface for engaging side walls of a cervical canal.

19. The insemination device of claim 18 in which said projection means comprises a spirally-extending rib.

20. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto; and expansion means disposed in said expansion chamber for absorbing fluid from said reservoir means and expanding so that said plunger is urged towards said proximal end of said member to cause discharge of semen from said semen chamber through said passageway of said nipple; said cervical cap including release means for minimizing surface adhesion between said cervical cap and a cervix.

21. The insemination device of claim 20 in which said release means comprises a plurality of holes formed in said cervical cap.

22. A time-release insemination device comprising:

a dome-shaped cervical cap adapted to conform and adhere to a cervix and having a peak portion at one end and a generally circular periphery at the other end;

an elongated tubular nipple defining a passageway and extending from said peak portion of said cap in a generally axial direction towards said circular periphery;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

reservoir means connected to said tubular member and in fluid communication with said expansion chamber for providing a quantity of fluid thereto; and expansion means disposed in said expansion chamber for absorbing fluid from said reservoir means and expanding so that said plunger is urged towards said proximal end of said member to cause discharge of semen from said semen chamber through said passageway of said nipple, said cervical cap being comprised of a biodegradable or water-soluble material which is operable to sufficiently degrade or dissolve so that said cervical cap will release from a cervix once a predetermined time period has elapsed.

23. The insemination device of claim 22 in which said biodegradable or water-soluble material comprises polyvinyl alcohol.

24. A time-release insemination device comprising:

an elongated tubular nipple defining a passageway;

means for positioning said tubular nipple adjacent to a cervix;

an elongated tubular member having proximal and distal ends and defining a semen chamber at said proximal end which is in fluid communication with said passageway of said nipple and defining an expansion chamber at said distal end;

a plunger slidably mounted in said tubular member for axial movement therein and positioned to separate said semen chamber from said expansion chamber;

a resilient and collapsible reservoir connected to said tubular member and in fluid communication with said expansion chamber for providing a quantity of fluid thereto; and expansion means disposed in said expansion chamber for absorbing fluid from said reservoir and expanding so that said plunger is urged towards said proximal end of said member to cause discharge of semen from said semen chamber through said passageway of said nipple.

25. The insemination device of claim 24 in which sealable aperture means are provided in communication with said expansion chamber and said reservoir for allowing withdrawal or introduction of fluids from or into said expansion chamber and said expansion means.

26. The insemination device of claim 25 in which said reservoir means defines a volume and is operable between a collapsed state in which said volume is evacuated and an expanded state in which said volume is filled with a fluid; wherein withdrawal of fluid through said sealable aperture means evacuates said volume so that said reservoir means assumes said collapsed state and also draws said plunger in said tubular member towards its distal end, thereby creating a negative pressure in said semen chamber and said passageway of said nipple for drawing semen into said passageway and said semen chamber.

27. The insemination device of claim 25 in which, when said reservoir means is in said collapsed state, introduction of fluid through said sealable aperture means fills said volume of said reservoir means so that it resumes said expanded state without causing movement of said plunger within said tubular member.

28. The insemination device of claim 27 in which said sealable aperture means comprises a self-sealing element.

29. The insemination device of claim 25 in which said reservoir means defines a volume and is operable between a collapsed state in which said volume is evacuated and an expanded state in which said volume is filled with a fluid and said sealable aperture means comprises a self-sealing element and a unidirectional valve;

wherein, when said reservoir means is in said expanded state, said reservoir means is collapsible so that said volume is evacuatable through said unidirectional valve and, when said reservoir means is in said collapsed state, said reservoir means is resiliently expandable upon release so that it draws said plunger in said tubular member towards its distal end, thereby creating a negative pressure in said semen chamber and said passageway of said nipple for drawing semen into said passageway and said semen chamber.

30. The insemination device of claim 29 in which, when said reservoir means is in said expanded state or said partially expanded state, introduction of fluid through said self-sealing element causes fluid in said reservoir means to be evacuated through said unidirectional valve so that said introduced fluid replaces said fluid in said reservoir means.

31. The insemination device of claim 24 in which said nipple has a cylindrical exterior surface and projection means are disposed on said exterior surface for engaging side walls of a cervical canal.

32. The insemination device of claim 31 in which said projection means comprises a spirally-extending rib.

33. The insemination device of claim 24 in which said expansion means causes said semen to be discharged through said nipple for at least 3 hours.

34. The insemination device of claim 24 in which said expansion means causes said semen to be discharged through said nipple for a period of about 6–8 hours.

\* \* \* \* \*